(12) United States Patent
Friemel et al.

(10) Patent No.: US 8,480,600 B2
(45) Date of Patent: Jul. 9, 2013

(54) METHOD AND APPARATUS FOR FEEDBACK CONTROL OF HIFU TREATMENTS

(75) Inventors: Barry Friemel, Redmond, WA (US);
Jessica E. Parsons, Kirkland, WA (US);
Charles D. Emery, Issaquah, WA (US);
Gregory P. Darlington, Snohomish, WA (US); Justin A. Reed, Seattle, WA (US);
Tim Etchells, Bothell, WA (US)

(73) Assignee: Mirabilis Medica Inc., Bothell, WA (US)

( * ) Notice: Subject to any disclaimer, the term of this patent is extended or adjusted under 35 U.S.C. 154(b) by 276 days.

(21) Appl. No.: 12/606,129

(22) Filed: Oct. 26, 2009

(65) Prior Publication Data
US 2010/0106019 A1    Apr. 29, 2010

Related U.S. Application Data

(60) Provisional application No. 61/108,435, filed on Oct. 24, 2008.

(51) Int. Cl.
*A61B 8/00* (2006.01)

(52) U.S. Cl.
USPC .................................. 601/2; 600/439; 604/22

(58) Field of Classification Search
USPC ............................................. 600/439; 601/2
See application file for complete search history.

(56) References Cited

U.S. PATENT DOCUMENTS

| | | | |
|---|---|---|---|
| 3,470,868 A | 10/1969 | Krause |
| 3,480,002 A | 11/1969 | Flaherty |
| 3,676,584 A | 7/1972 | Plakas |
| 4,097,835 A | 6/1978 | Green |
| 4,185,502 A | 1/1980 | Frank |
| 4,282,755 A | 8/1981 | Gardineer |
| 4,347,850 A | 9/1982 | Kelly-Fry |

(Continued)

FOREIGN PATENT DOCUMENTS

| | | |
|---|---|---|
| EP | 0 614 651 A1 | 9/1994 |
| EP | 0 734 742 A2 | 10/1996 |

(Continued)

OTHER PUBLICATIONS

International Search Report and Written Opinion mailed Jun. 8, 2010, issued in corresponding International Application No. PCT/US2009/062127, filed Oct. 26, 2009, 6 pages.

(Continued)

*Primary Examiner* — Parikha Mehta
(74) *Attorney, Agent, or Firm* — Christensen O'Connor Johnson Kindness PLLC

(57) ABSTRACT

HIFU therapy to a desired tissue site is controlled based on detected changes in one or more characteristics of a received backscatter signal resulting from exposure of the tissue to HIFU or other interrogation signals. In one embodiment, the bloom of backscatter signals outward from a treatment region (e.g., towards the HIFU transducer) is detected and monitored. Once the bloom reaches a predetermined location, treatment is stopped. Other signal characteristics such as angular distribution of frequency components in the backscatter signal, changes in reflection, power required to saturate a tissue characteristic, changes in attenuation and changes in a cumulative energy distribution function of the backscatter signal that change as a result of the application of HIFU power are also used to control the delivery of HIFU signals in accordance with other embodiments of the disclosed technology.

17 Claims, 10 Drawing Sheets

U.S. PATENT DOCUMENTS

| | | | |
|---|---|---|---|
| 4,484,569 A | 11/1984 | Driller |
| 4,742,829 A | 5/1988 | Law |
| 4,819,621 A | 4/1989 | Ueberle |
| 4,835,689 A | 5/1989 | O'Donnell |
| 4,855,911 A | 8/1989 | Lele |
| 4,858,613 A | 8/1989 | Fry |
| 4,893,624 A | 1/1990 | Lele |
| 4,932,414 A | 6/1990 | Coleman |
| 5,005,579 A | 4/1991 | Wurster |
| 5,036,855 A | 8/1991 | Fry |
| 5,070,879 A | 12/1991 | Herres |
| 5,080,101 A | 1/1992 | Dory |
| 5,080,102 A | 1/1992 | Dory |
| 5,391,140 A | 2/1995 | Schaetzle |
| 5,471,988 A | 12/1995 | Fujio |
| 5,665,054 A | 9/1997 | Dory |
| 5,769,790 A | 6/1998 | Watkins |
| 5,810,007 A | 9/1998 | Holupka |
| 6,042,556 A | 3/2000 | Beach |
| 6,071,239 A | 6/2000 | Cribbs |
| 6,126,607 A | 10/2000 | Whitmore, III |
| 6,128,522 A | 10/2000 | Acker |
| 6,196,972 B1 | 3/2001 | Moehring |
| 6,267,734 B1 | 7/2001 | Ishibashi |
| 6,508,774 B1 | 1/2003 | Acker |
| 6,632,177 B1 | 10/2003 | Phillips |
| 6,645,162 B2 | 11/2003 | Friedman |
| 6,666,822 B2 | 12/2003 | Agano |
| 6,716,184 B2 | 4/2004 | Vaezy |
| 6,719,694 B2 | 4/2004 | Weng |
| 6,840,936 B2 | 1/2005 | Sliwa, Jr. |
| 7,061,381 B2 | 6/2006 | Forcier |
| 7,063,666 B2 | 6/2006 | Weng |
| 7,175,596 B2 | 2/2007 | Vitek |
| 7,258,674 B2 | 8/2007 | Cribbs |
| 7,286,499 B2 | 10/2007 | Tiedemann, Jr. |
| 7,452,357 B2 | 11/2008 | Vlegele |
| 7,470,241 B2 | 12/2008 | Weng |
| 7,492,666 B2 | 2/2009 | Scoca |
| 7,674,630 B2 | 3/2010 | Siversson |
| 7,824,336 B2 | 11/2010 | Kawabata |
| 7,993,289 B2 | 8/2011 | Quistgaard |
| 8,016,757 B2 | 9/2011 | Kaczkowski |
| 2001/0017848 A1 | 8/2001 | Tiedemann, Jr. |
| 2002/0147397 A1 | 10/2002 | Agano |
| 2003/0028111 A1 | 2/2003 | Vaezy |
| 2003/0149380 A1 | 8/2003 | Fujimoto |
| 2003/0189488 A1 | 10/2003 | Forcier |
| 2004/0030268 A1 | 2/2004 | Weng |
| 2004/0039312 A1 | 2/2004 | Hillstead |
| 2004/0153126 A1 | 8/2004 | Okai |
| 2005/0107702 A1 | 5/2005 | He |
| 2005/0154431 A1 | 7/2005 | Quistgaard |
| 2005/0281444 A1 | 12/2005 | Lundberg |
| 2006/0056273 A1 | 3/2006 | Scoca |
| 2007/0016042 A1 | 1/2007 | Kawabata |
| 2007/0083120 A1 | 4/2007 | Cain |
| 2007/0106157 A1* | 5/2007 | Kaczkowski et al. ......... 600/438 |
| 2007/0239007 A1 | 10/2007 | Silverman |
| 2007/0255267 A1 | 11/2007 | Diederich |
| 2007/0270792 A1 | 11/2007 | Hennemann |
| 2008/0058683 A1 | 3/2008 | Gifford |
| 2008/0154131 A1 | 6/2008 | Lee |
| 2008/0217259 A1 | 9/2008 | Siversson |
| 2008/0253525 A1 | 10/2008 | Boyden |
| 2010/0036292 A1 | 2/2010 | Darlington |

FOREIGN PATENT DOCUMENTS

| | | |
|---|---|---|
| EP | 1 757 244 A1 | 2/2007 |
| GB | 2 279 742 A | 1/1995 |
| WO | 93/17646 A2 | 9/1993 |
| WO | 95/01126 A1 | 1/1995 |
| WO | 01/82777 A2 | 11/2001 |
| WO | 2005/000097 A2 | 1/2005 |
| WO | 2006/129099 A1 | 12/2006 |

OTHER PUBLICATIONS

Rabkin, B.A., et al.,"Hyperecho in Ultrarsound Images of HIFU Therapy: Involvement of Cavitation," Ultrasound in Medicine and Biology 31(7):947-956, 2005.

Delon-Martin, C., et al., "Venous Thrombosis Generation by Means of High-Intensity Focused Ultrasound," Ultrasound in Medicine & Biology 21(1):113-119, 1995.

Enholm, J.K., et al., "Improved Volumetric MR-HIFU Ablation by Robust Binary Feedback Control," IEEE Transactions on Biomedical Engineering 57(1):103-113, Jan. 2010.

Friedland, F., "Ultrasonic Therapy," American Journal of Nursing 59(9):1272-1275 (plus 1 additional page), Sep. 1959.

Fry, F.J., "Recent Bioeffects With Ultrasound on the Reproductive System and Solid Tumors," Journal of the Acoustical Society of America 63(Suppl. 1):S13 (plus 1 additional page), May 1978.

Mougenot, C., et al., "Automatic Spatial and Temporal Temperature Control for MR-Guided Focused Ultrasound Using Fast 3D MR Thermometry and Multispiral Trajectory of the Focal Point," Magnetic Resonance in Medicine 52(5):1005-1015, 2004.

Mougenot, C., et al., "Three-Dimensional Spatial and Temporal Temperature Control With MR Thermometry-Guided Focused Ultrasound (MRgHIFU)," Magnetic Resonance in Medicine 61(3):603-614, Mar. 2009.

Ngo, F.C., et al., "An Experimental Analysis of a Sector-Vortex Phased Array Prototype," Proceedings of IEEE Ultrasonics Symposium, Montreal, Oct. 3-6, 1989, vol. 2, pp. 999-1002.

Orsini-Meinhard, K., "UW Tech-Transfer Program Putting Discoveries to Work," The Seattle Times, May 27, 2007, 8 pages.

Rabkin, B.A., et al., "Biological and Physical Mechanisms of HIFU-Induced Hyperecho in Ultrasound Images," Ultrasound in Medicine & Biology 32(11):1721-1729, Nov. 2006.

Sanghvi, N.T., "High Intensity Focused Ultrasound (HIFU) for the Treatment of Rectal Tumors: A Feasibility Study," Proceedings of IEEE Ultrasonics Symposium, Cannes, France, Oct. 31-Nov. 3, 1994, vol. 3, pp. 1895-1898.

"ThermoDox™ Animal Studies to Be Presented at 6th International Symposium on Therapeutic Ultrasound in Oxford, England," Aug. 30-Sep. 2, 2006, Celsion, Inc.,<http://www.celsion.com/news/releasedetail.dfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Umemura, S.-I., and C.A. Cain, "Acoustical Evaluation of a Prototype Sector.-Vortex Phased-Array Applicator," IEEE Transactions on Ultrasonics, Ferroelectrics, and Frequency Control 39(1):32-38, Jan. 1992.

Vaezy, S., et al., "Image-Guided Acoustic Therapy," Annual Review of Biomedical Engineering 3:375-390 (plus 4 additional pages), Aug. 2001.

Zanelli, C.I., et al., "Design and Characterization of a 10 cm Annular Array Transducer for High Intensity Focused Ultrasound (HIFU) Applications," Proceedings of the IEEE Ultrasonics Symposium, Cannes, France, Oct. 31-Nov. 3, 1994, vol. 3, pp. 1887-1890.

International Search Report and Written Opinion mailed May 18, 2010, issued in corresponding International Application No. PCT/US2009/053050, filed Aug. 6, 2009, 15 pages.

European Search Report mailed Dec. 13, 2012, in European Application No. 09822853.9, filed Oct. 26, 2009, 7 pages.

* cited by examiner

DISTANCE (D) TO LEADING EDGE OF BACKSCATTER
DECREASES DURING TREATMENT ($D_{INITIAL} > D_{FINAL}$)

LESION LENGTH (L) GROWS TOWARD TRANSDUCER
DURING TREATMENT ($L_{FINAL} > L_{INITIAL}$)

RATIO OF 2ND HARMONIC FUNDAMENTAL AS A FUNCTION OF ANGLE TO THE RECEIVING APERATURE

METHOD AND APPARATUS FOR FEEDBACK CONTROL OF HIFU TREATMENTS

CROSS-REFERENCE TO RELATED APPLICATION

This application claims the benefit under 35 U.S.C. Section 119(e) of U.S. Provisional Application No. 61/108,435 filed Oct. 24, 2008, which is herein incorporated by reference in its entirety.

BACKGROUND

As an alternative to surgical treatment of pathological tissue wherein the diseased region is physically removed from the body, there is an increased interest in treating tissue in situ with a minimally invasive process. One such process that can selectively treat diseased tissue in a non-invasive manner is high intensity focused ultrasound (HIFU). With HIFU, high intensity acoustic signals are directed at a target treatment site in order to subject the tissue to a rapid increase in temperature and/or to mechanical destruction due to interaction with the applied acoustic signals. The treated tissue may form one or more "lesions" that are typically left in the body and may be absorbed through normal physiological processes.

When HIFU therapy is applied to a desired tissue site, variations in tissue depth and other properties such as diffraction, attenuation, sound speed, or other tissue-related parameters along the acoustic propagation path affect the amount of energy deposited. These variations cause corresponding variations in the size and nature of the resulting lesions created. Treatment regimens that are solely based on applying a predetermined dose of HIFU energy may therefore achieve inconsistent results due to these variations.

As an example, the transabdominal treatment of uterine fibroids with HIFU requires passing acoustic HIFU energy through multiple tissue layers of varying depth that have diverse properties (e.g. skin, fat, muscle, fluid in bladder, uterine wall and the fibroid itself). If not carefully controlled, the application of HIFU energy to the treatment site may cause undesired damage to tissue surrounding the fibroid as well as inconsistent results within the treatment site.

Prior art in the field of "cavitation detection" has included monitoring the amplitude and/or energy of bubble reflections in an attempt to monitor the progression of HIFU treatment. One typical implementation of cavitation detection in prior art is to halt or reduce application of HIFU power upon the first instance of bubble detection at any point along the treatment path, in order to avoid distorted or exaggerated lesion volumes that often result from the onset of uncontrolled cavitation or boiling. However, this usage can severely limit the efficacy of resultant HIFU lesions because this type of indiscriminant bubble detection without regard for the spatial distribution of such bubbles can result in premature cessation of HIFU power long before the lesion has filled the desired target volume.

Another proposed technique used in prior art involves the use of standard imaging ultrasound to monitor the "hyperecho" (i.e. reflections off bubbles in the tissue that are displayed as regions of enhanced brightness on standard B-mode ultrasound images). Visual observation of the hyperecho, however, does not quantify the amplitude or energy of the signal reflected from a given region and is therefore also unreliable in predicting the location and extent of the HIFU lesions created.

Finally, some HIFU therapies rely on MRI to monitor temperature as a proxy for HIFU lesion formation. However, this method is extremely expensive (MRI systems typically cost $1-3M), it is not real time since several seconds are required between MRI acquisitions, and the measured temperature is not considered accurate enough to automatically control HIFU parameters such as treatment duration.

Given these problems, there is a need for a more reliable and cost effective method to monitor the formation of HIFU lesions at varying depths and in tissue with statically or dynamically varying properties.

SUMMARY

To address the above mentioned problems and others, the technology disclosed herein is a feedback mechanism for a HIFU therapy system that operates to predict when treatment of a desired tissue site is complete or is potentially spreading to tissue beyond the treatment site. In one embodiment, the feedback mechanism operates to limit the total energy delivered to the tissue site by stopping treatment or otherwise modifying one or more HIFU parameters (i.e. therapy transducer acoustic power) when it is detected that a lesion is progressing outside the bounds of the intended treatment region (e.g., into a pre-focal area located proximal to the HIFU transducer).

In accordance with one embodiment of the disclosed technology, the feedback mechanism is based on "bloom detection". Bloom is a general term describing a change in the properties of HIFU treated tissue that grow outward from the treatment region over time. A bloom signal is a signal created in response to the HIFU signals transmitted from either a HIFU transducer or some other special-purpose transmitter. The bloom signal is received at either the HIFU transducer or another special-purpose receiver. The disclosed technology uses techniques that detect and monitor the extent of the bloom and that use the information to control the subsequent application of HIFU energy.

In one embodiment, echo signals (e.g. backscatter signals) that are created in response to applied HIFU signals are detected and analyzed to determine an amount of energy delivered to a location within the body. In one embodiment, the bloom signal is a leading edge of an averaged backscatter signal that is detected and monitored as it moves towards the HIFU transducer. Once the leading edge reaches a predetermined location where it is desired to stop treatment, the HIFU treatment is stopped or reduced in power.

The bloom signal can be comprised of high-amplitude acoustic signals passively reflecting and/or actively emanating from boiling or cavitation activity. This class of bloom signal results from the presence of gas or vapor bodies in the tissue that arise from the combined mechanical and thermal effects of HIFU application. However, the bloom signal is not limited to the detection of bubble-related activity. The bloom signal can also be created due to other HIFU-induced effects in the tissue such as, but not limited to, changes in stiffness, speed of sound, diffraction, attenuation, harmonic content and/or reflectivity due to non-bubble causes.

In another embodiment, the bloom signal does not physically migrate outward during treatment (e.g., move toward the transducer), but instead is reflected in some change in a characteristic of the received backscatter signal. For example, in another embodiment, the harmonic content of the reflected signal is detected and monitored during treatment. Once the harmonic content reaches a certain value or ratio at a particular spatial location, then treatment is halted.

In another embodiment, the applied HIFU causes the angular distribution of the frequency components in the backscatter signals to change. The angular distribution of the backscatter signal is measured during treatment and treatment is halted when the angular distribution reaches a particular value or if the distribution changes by more than a particular value.

In another embodiment, the attenuation of the tissue in the treatment site changes with applied HIFU. The attenuation is measured during treatment and treatment is modified when the attenuation reaches a threshold or varies by more than a threshold amount.

In yet another embodiment, the power of the HIFU signal required to saturate a characteristic of the backscatter signal changes with applied HIFU. The power level required to saturate the characteristic is measured and treatment is modified when the power level required reaches a threshold or varies by more than a threshold amount.

In still another embodiment of the disclosed technology, the cumulative energy distribution function (i.e. the accumulated backscatter energy of the HIFU signals as a function of depth) of the tissue at the treatment site varies with applied HIFU. The cumulative energy distribution function is calculated and monitored during treatment. Once the energy absorbed at a predetermined location reaches a threshold or the cumulative energy distribution function changes by more than a threshold amount, treatment is modified.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
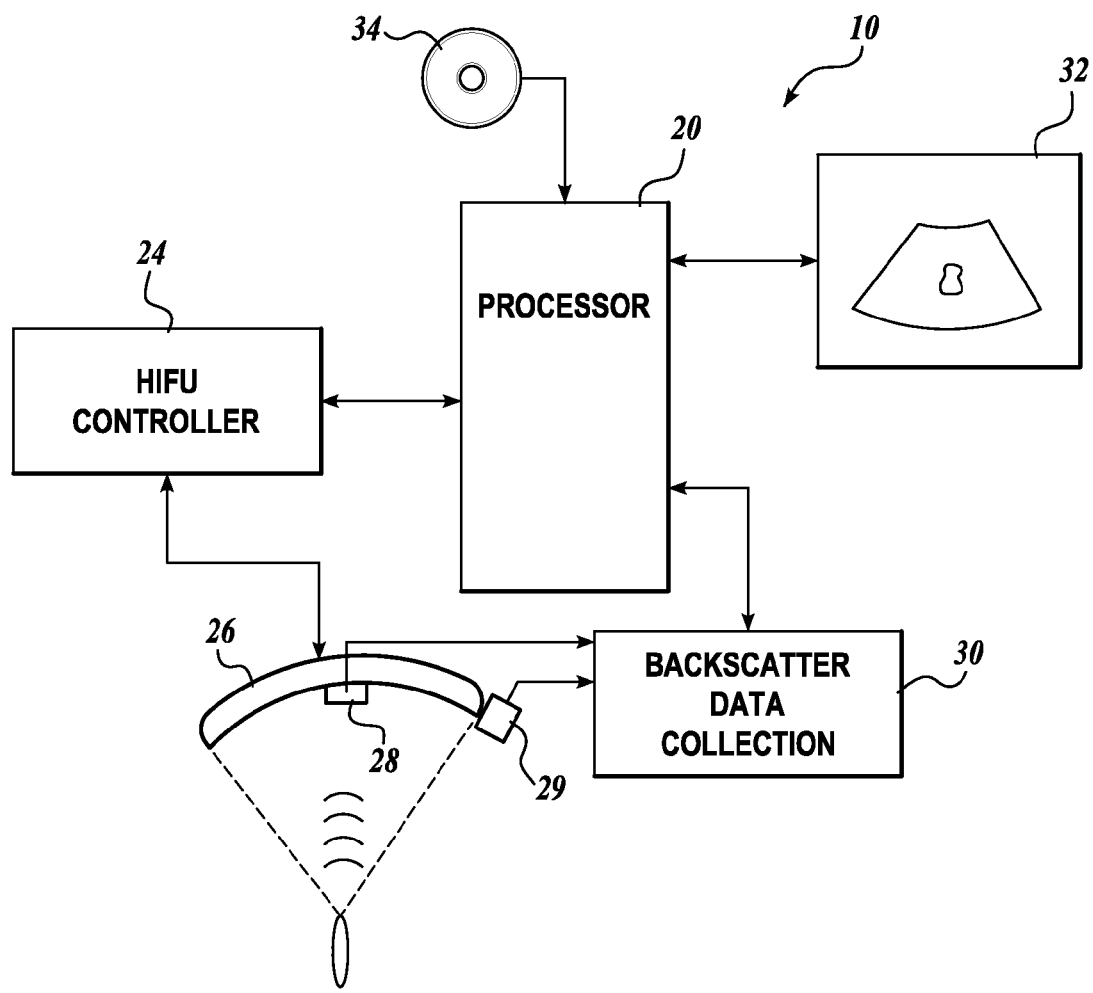
FIG. 1 illustrates a block diagram of a HIFU treatment system in accordance with one embodiment of the disclosed technology.

The technology disclosed herein uses a transducer to detect changes in echo signals due to the application of HIFU energy that is applied to a treatment site. A processor analyzes these changes in order to determine when treatment is complete and to assess the spatial extent of a HIFU lesion along or at an arbitrary angle to the acoustic beam axis. In one embodiment, the technology relates to a method of detecting, acquiring, and processing echo signals created by acoustic transmitter(s)/receiver(s) in response tissue changes due to HIFU application in a manner that produces useful human perceptible and/or automatic feedback signals to indicate how thoroughly a treatment region has been treated. HIFU therapy can be stopped or modified by use of this feedback signal so as to produce more consistent therapeutic effects regardless of variations in the propagation path or local tissue parameters.

In several of the embodiments described below, the delivery of HIFU signals to a treatment site is controlled based on detected HIFU-related changes in tissue properties. For instance, HIFU-induced gas or vapor bubbles can contribute to an increased reflectivity of HIFU signals, both of which tend to migrate toward the HIFU transducer as the treatment progresses. However, the disclosed technology is not limited to detection of bubble-related activity, since HIFU can induce a variety of other changes that may be detectable by analyzing the reflected HIFU signal. Such changes may include (but are not limited to) changes in stiffness, speed of sound, diffraction, attenuation, harmonic content, and/or reflectivity due to non-bubble causes. Monitoring the changes in a backscatter signal created in response to applied HIFU signals (including measures related to both its energy and location) is referred to herein as "bloom detection."

This technology described herein also provides the ability to remotely assess the resultant lesion dimension along or at an arbitrary angle to the acoustic axis by quantifying the spatial extent of a reflected signal, including (but not limited to) its extent proximal to the treatment site. This feature can be used to non-invasively estimate lesion sizes (e.g. lesion lengths or volumes). This application of bloom detection to non-invasively assess the physical extent of the developing lesion provides an advantage over conventional ultrasound imaging techniques, which typically lack sufficient sensitivity to distinguish HIFU lesions from surrounding undamaged tissue. By monitoring the position and amplitude (or related metrics) of a leading edge of a backscatter signal throughout treatment, the spatial extent of the treated tissue region can be tracked in real-time.

In one embodiment, the disclosed technology uses a transducer to receive HIFU energy reflected from the treatment region. Signals produced by the transducer are analyzed with a computer or other programmed processor to determine when treatment is complete and to assess the spatial extent of the HIFU lesion. The signal representing the reflected HIFU energy is further used to limit the total energy delivered to the treatment region, by stopping or modifying the treatment when regions proximal to the treatment site are detected to contain increased energy.

FIG. 1 illustrates a block diagram of a HIFU ultrasound treatment system that can be used to implement the disclosed technology. The system 10 includes a computer 20, which may be a stand alone or networked computer system. The computer 20 includes one or more processors that are programmed to implement the techniques described in detail below. As will be appreciated by those of ordinary skill in the art, the computer 20 (or processors) may be incorporated within an ultrasound signal processor. The computer 20 is in communication with a HIFU controller 24 that produces the driving signals applied to a HIFU transducer 26. The HIFU transducer 26 generates corresponding HIFU signals that are directed to a treatment zone of the transducer. The transducer may have a fixed treatment zone or a treatment zone that is mechanically or electrically steerable. In addition, the HIFU transducer may be steered with a mechanical wobbler that causes the treatment zone to move in a pattern while creating lesions. In one embodiment, the treatment zone of the HIFU transducer 26 is moved in a circular pattern around the perimeter of an elemental treatment volume to be created at a treatment site as HIFU energy is being applied in order to directly ablate the perimeter and indirectly ablate the center of a treatment site by thermal conduction. A suitable mechanical wobbler and method of creating HIFU lesions are disclosed in U.S. patent application Ser. No. 12/573,840, which is herein incorporated by reference. In this instance, the backscatter signals can be monitored as the treatment zone is moved along the path of a repeated geometric pattern or around the perimeter of some elemental treatment volume (e.g. a circle). The backscatter signals may be continually processed, periodically sampled, and/or spatially averaged (e.g. over the course of a repeating geometric pattern).

In some embodiments, the HIFU transducer 26 and HIFU controller 24 can also detect backscatter signals created in response to an applied HIFU signal.

In response to an applied HIFU signal, the tissue being treated produces a backscatter signal that is detected by a second ultrasound transducer 28. In one embodiment, the second transducer 28 is a polyvinylidene fluoride (PVDF) transducer is mounted in the center of a HIFU transducer 26 and is used to receive reflected acoustic energy (e.g. the backscatter signal) from the treatment region. In this embodiment, the HIFU transducer 26 delivers ultrasound energy (one or more therapy pulses) to the treatment site to provide a therapeutic effect. HIFU (or interrogational energy from an alternate acoustic transmitter) is reflected from the treatment site with varying intensities at different depths due to variations in the tissue parameters and local changes in the tissue resulting from the incident HIFU pulses. The backscatter signal is detected by the PVDF transducer that generates a corresponding electrical signal that is passed to a backscatter data collection system 30 including conventional ultrasound signal processing hardware (preamplifiers, filters, A/D converters etc.). The backscatter data collection system 30 receives and digitizes the detected backscatter signals for analysis by the computer 20. The computer 20 analyzes the detected backscatter signals and produces control signals that are fed to the HIFU controller 24 to adjust and/or stop the delivery of HIFU signals in feedback loop. Alternatively, the control signals produced by the computer 20 can be used to trigger an audible or visual alarm for the physician so that he or she can manually halt or reduce the power of the HIFU treatment.

The system also includes a display 32 where a physician can view the treatment process. A computer readable storage media 34 includes instructions that are executable by the processors of the computer system 20 to implement the technology described. The computer readable storage media 32 may be a CD, DVD, hard drive, flash drive or a wired or wireless communication link etc.

In another embodiment, the backscatter HIFU energy reflected from the treatment site is received by the HIFU transducer 26 itself (rather than separate PVDF transducer) and then passed to a data collection system 30.

In still another embodiment, the reflected HIFU energy is received by one or more separate ultrasound receivers 29 (i.e. other than a PVDF or HIFU transducer), such as a single imaging transducer element, or array of imaging transducer elements. The array of transducer elements may be clustered together in a defined region relative to the therapy transducer (e.g. imaging array) or the array of transducer elements may be spread over a significantly larger region such that multiple receive angles may be used to interrogate the treatment site. In all of these cases, the received backscatter HIFU signal generates a corresponding electrical signal that may be passed to the backscatter data collection system 30 and analyzed by the computer 20. The received electrical signal is processed to provide feedback as to when the treatment is complete.

In the case where backscattered signals are received by an imaging transducer, rather than processing the received signals directly, the resulting image produced by the imaging transducer can be processed to determine when treatment should be halted. The leading edge of the backscatter signal may be monitored by detecting the change in brightness in each pixel of the image of the pre-focal region. This could be done visually, but more preferably via a computer processor, which quantifies the change in brightness of each displayed pixel and integrates this change within some region of pixels over a period of time.

Figure 2A:
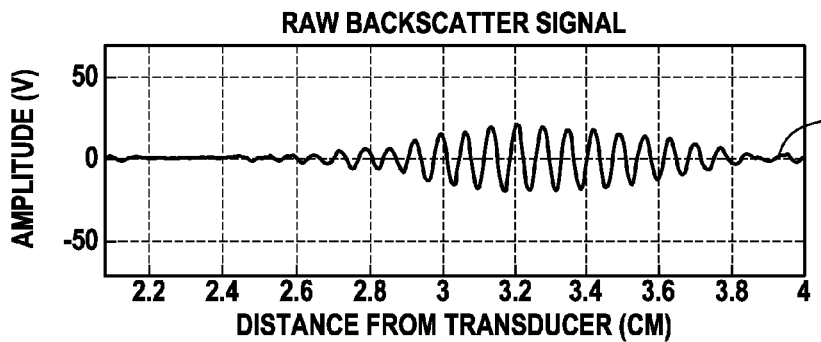
FIG. 2A illustrates a raw, reflected backscatter signal created in response to an applied HIFU signal.

FIG. 2A illustrate a graph of the amplitude of a reflected backscatter signal 50 versus depth from the HIFU transducer. In the example shown, it can be seen that the backscatter signal has a maximum amplitude at approximately 3.2 cm. in depth due to the focused nature of the HIFU transducer. To detect the bloom of the backscatter signal 50, numerous backscatter signals from a set of HIFU firings are received, digitized and stored in a memory. The backscatter signals from each of the firings are envelope detected and averaged. In one embodiment, the leading edge of the averaged backscatter signal moves toward the HIFU transducer as HIFU treatment progresses. To control the application of HIFU energy, the movement of the leading edge is monitored and treatment is modified, i.e. halted, when either the leading edge has moved by more than a predetermined amount or when the energy applied to a predetermined location within the body has reached a threshold value.

Figure 2B:
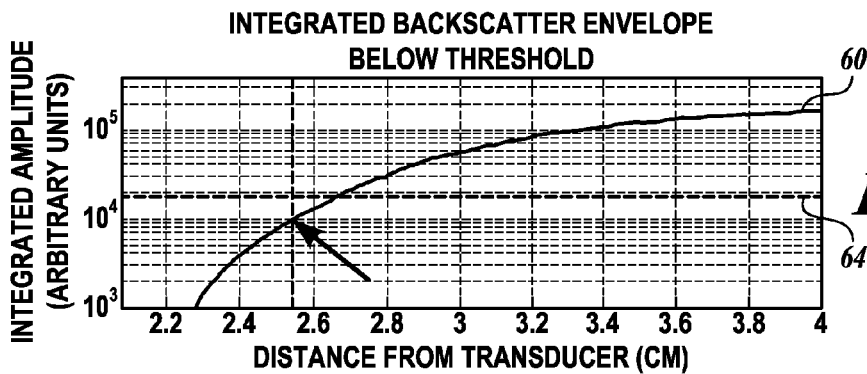
FIG. 2B illustrates an integrated backscatter envelope that is below a threshold level in accordance with one embodiment of the disclosed technology.

In one embodiment, the movement of the averaged backscatter signal toward the HIFU transducers is measured by integrating the averaged, envelope detected backscatter signals with the computer to produce information as shown in FIG. 2B. In this graph, the integrated backscatter signal 60 has a magnitude that grows with increasing depth of the tissue as the signal energy is integrated. This depth in tissue can be calculated based on the mean speed of sound and the time between HIFU pulse transmission and receipt of the corresponding backscatter signal.

To control the application of HIFU energy, the computer analyzes the magnitude of the integrated backscatter signal at a predefined depth. This depth is typically the upper (proximal) boundary of where the lesion being created should stop or where no further treatment should extend. In the example shown, the magnitude of the integrated backscatter signal 60 is determined for a depth of 2.55 cm which corresponds to the point at which it is desired to stop the lesion growth. In FIG. 2B, the magnitude of the integrated backscatter signal 60 at the desired depth is compared against a predetermined threshold 64. If the magnitude is less than the threshold 64, the computer 20 continues with the HIFU treatment.

Figure 2C:
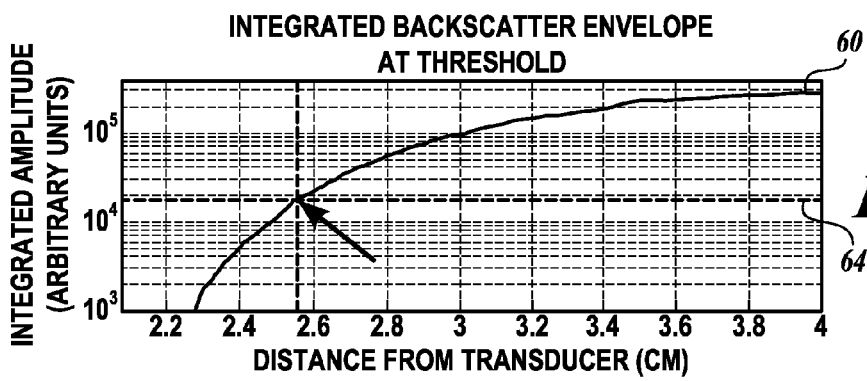
FIG. 2C illustrates an integrated backscatter envelope that is at a threshold level in accordance with an embodiment of the disclosed technology.

FIG. 2C is a graph that illustrates an example where the integrated backscatter signal 60 at a depth of 2.55 cm. has a magnitude that equals the predetermined threshold 64. In this case, the computer 20 can produce the feedback signal which is used to halt the HIFU treatment or reduce its power.

Figure 2D:
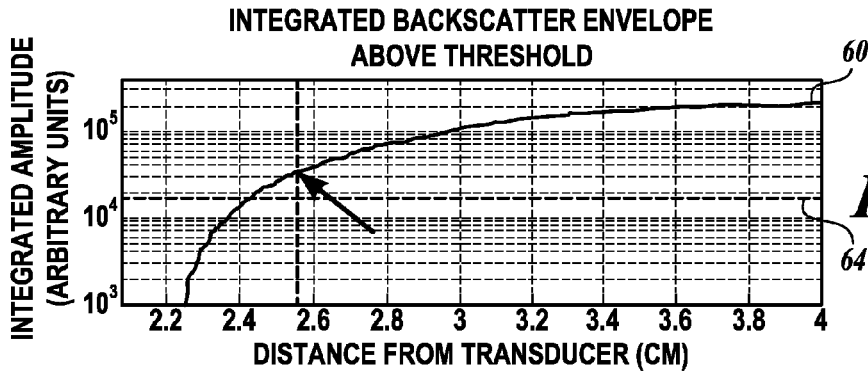
FIG. 2D illustrates an integrated backscatter envelope that is above a threshold level in accordance with an embodiment of the disclosed technology.

In FIG. 2D, a graph shows the integrated backscatter signal 60 with a magnitude at the depth of 2.55 cm. that exceeds the predetermined threshold 64, thereby indicating that the HIFU lesion has bloomed farther than desired. The resulting lesion will thus be larger than desired and less predictable/consistent in spatial extent.

As can be seen by viewing the graphs shown in FIGS. 2B-2D, the leading edge of the integrated backscatter signal is moving proximally toward the HIFU transducer. The control of the HIFU treatment can therefore also be controlled by detecting when a certain point on the integrated backscatter signal 60 reaches a predefined depth in the tissue.

Figure 3A:
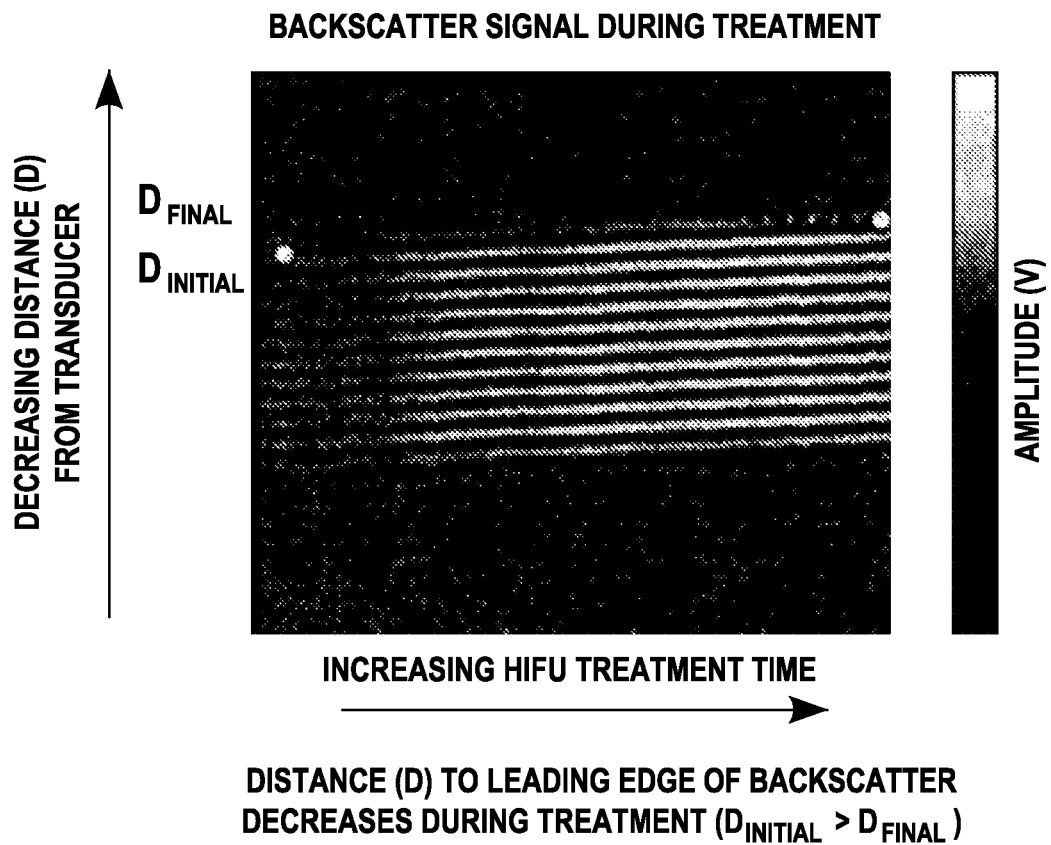
FIGS. 3A and 3B illustrate a plot of an acoustic backscatter signal that migrates over time, and the lesion growth corresponding to this signal migration, for use in controlling HIFU energy delivered to a treatment site in accordance with another embodiment of the disclosed technology.
Figure 3B:
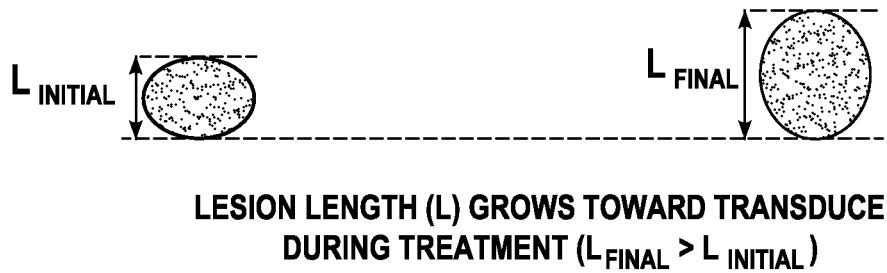

In the graph shown in FIG. 3A, a leading edge of a backscatter signal is shown as being received at a distance $D_{initial}$ from the HIFU transducer. As HIFU energy is continually applied, it can be seen in FIG. 3A that the leading edge of the backscatter signal moves toward the HIFU transducer so that after a period of time the leading edge is now located a distance, $D_{final}$, away from the HIFU transducer, where $D_{final}$ is less than $D_{initial}$ (i.e., closer to the transducer). Because the leading edge of the backscatter signal has now moved toward the HIFU transducer, the size of the lesion created has also increased from an initial length $L_{initial}$ to a final length $L_{final}$, as shown in FIG. 3B. The final lesion length $L_{final}$ is proportional to the difference between $D_{final}$ and $D_{initial}$. Therefore, by knowing the difference ($D_{final}-D_{initial}$) it is possible to estimate the length of the lesion created. When the length reaches a desired length, HIFU treatment can be halted. Note that this technique for lesion growth assessment would require separating any apparent backscatter shift due to temperature-dependent sound speed changes from the actual physical migration of the leading edge of the backscatter signal, so as not to overestimate the actual extent to which the lesion expands spatially over the course of the HIFU treatment.

The movement in the backscatter signals may be caused by a number of physical phenomena including dynamically changing bubbles, other cavitation activity or temperature changes. Regardless of the underlying physical cause, the large amplitude variations in the detected backscatter signal that are used to detect the movement are short lived and highly variable. Therefore in one embodiment, the backscatter signals are pre-processed to emphasize the large variations and reduce clutter.

Figure 4A:
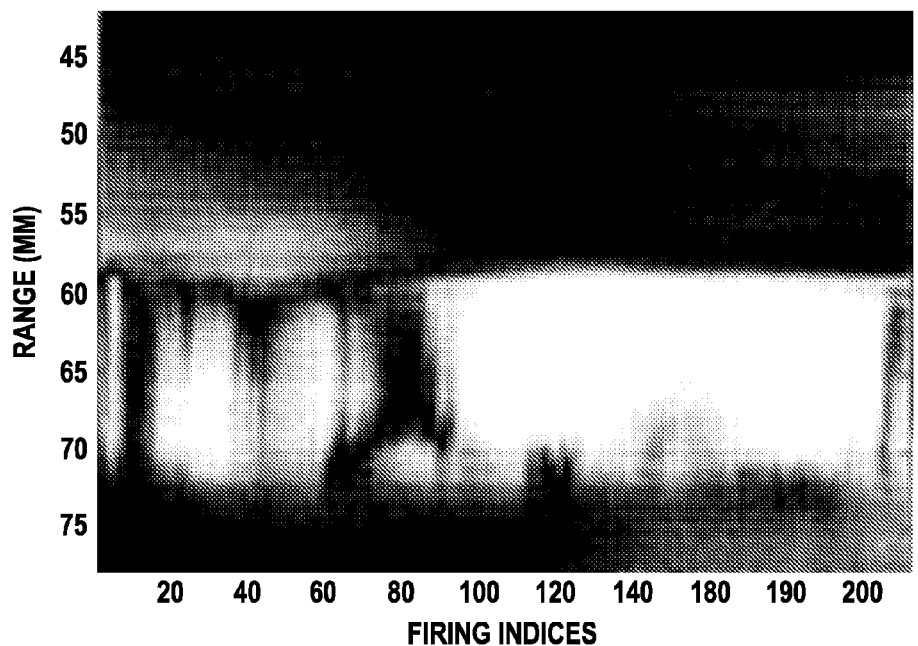
FIG. 4A illustrates a number of backscatter signal data for a number of HIFU firings that are used in bloom detection in accordance with the disclosed technology.

FIG. 4A illustrates a set of backscatter signals (vectors) that are detected in response to a group of 210 HIFU firings. Each vector records an amplitude of the detected backscatter signal at depths between 40 and 80 mm. away from the HIFU transducer. In the illustration shown, the amplitude is indicated by color where black represents low amplitude signals and white indicates high amplitude signals. As can be seen, the highest amplitude backscatter signals occur at approximately 58-65 mm. in depth between the 100th and 190th firings.

Figure 4B:
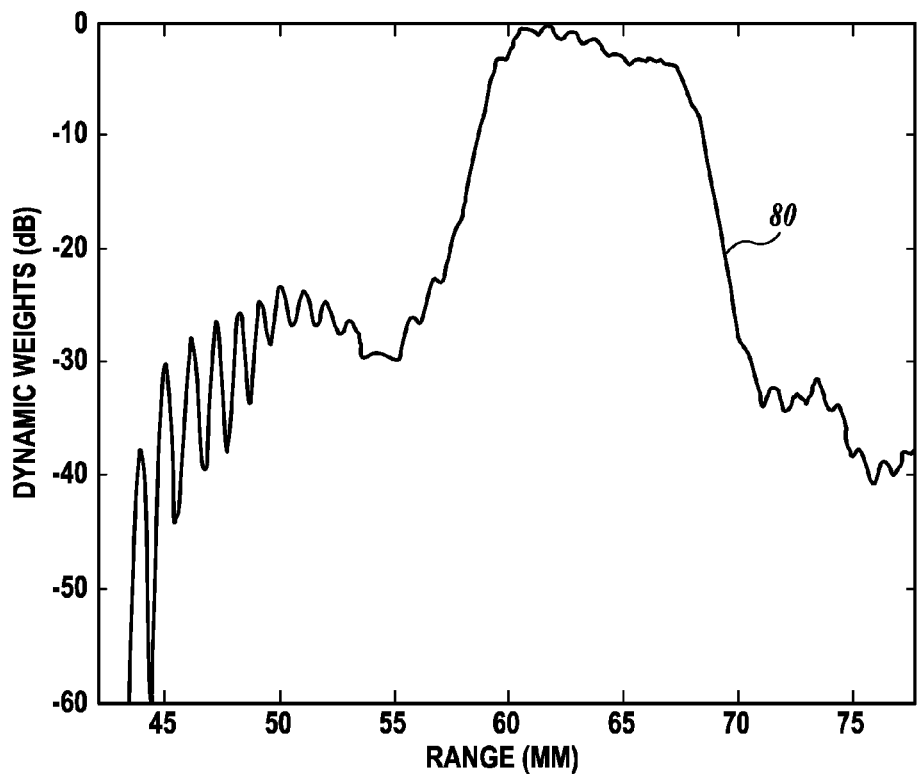
FIG. 4B illustrates a weighting function determined from the changes in amplitude of the backscatter signals versus depth for each of the signals shown in FIG. 4A in accordance with an embodiment of the disclosed technology.

To emphasize the high amplitude signals, a pair of weighting functions is determined from the detected backscatter signals. FIG. 4B illustrates a first weighting function that determines the depth where the highest change in amplitude is occurring. In one embodiment, a weighting function is determined by calculating the standard deviation of backscatter signal amplitude at each depth and normalizing the results. For the backscatter signals shown in FIG. 4A, the resulting weighting function 80 is shown in FIG. 4B. As can be seen the weighting function 80 has a peak between 58-65 mm. corresponding to the depth where the change in amplitude (variance) of the backscatter signal is the greatest.

Figure 4C:
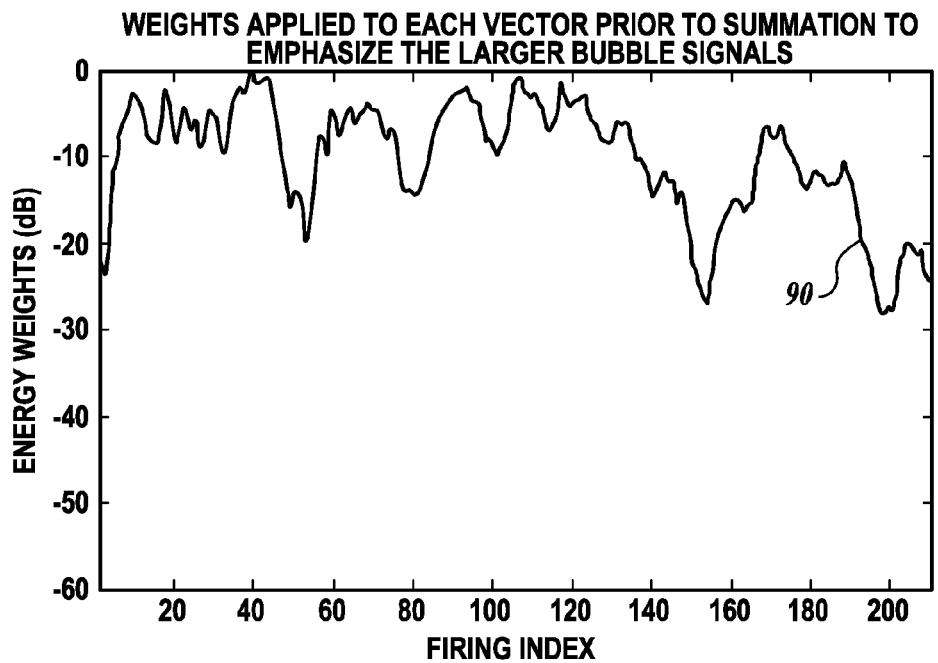
FIG. 4C illustrates a weighting function determined from the energy in each backscatter signal detected in FIG. 4A.

In addition to determining the depth where the change in amplitude of the backscatter signals is the greatest, one embodiment of the disclosed technology also determines the vectors of backscatter signals that have the greatest energy. To compute this, the RMS power of each vector is determined, and normalized for each HIFU firing. FIG. 4C illustrates a weighting function 90 produced from the backscatter signals shown in FIG. 4A.

Figure 4D:
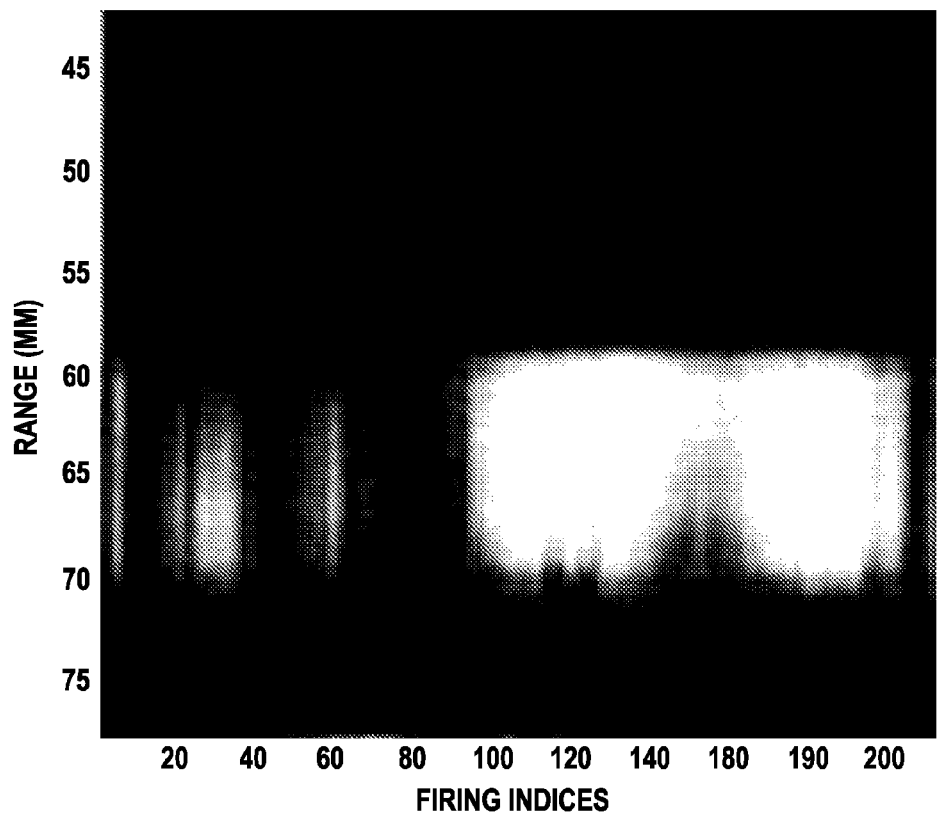
FIG. 4D illustrates the backscatter signals shown in FIG. 4A after weighting with the weighting functions shown in FIGS. 4B and 4C.

After computing the weighting functions, they are used to scale the detected backscatter signals in order to emphasize the high variance/high energy regions and depress the low variance/low energy regions. Applying the weighting functions 80 and 90 to the vectors shown in FIG. 4A results in the weighted backscatter signals shown in FIG. 4D. The resulting vectors are then averaged for each firing to produce a composite envelope detected, averaged backscatter signal that is sufficiently stable for use in bloom detection.

Figure 4E:
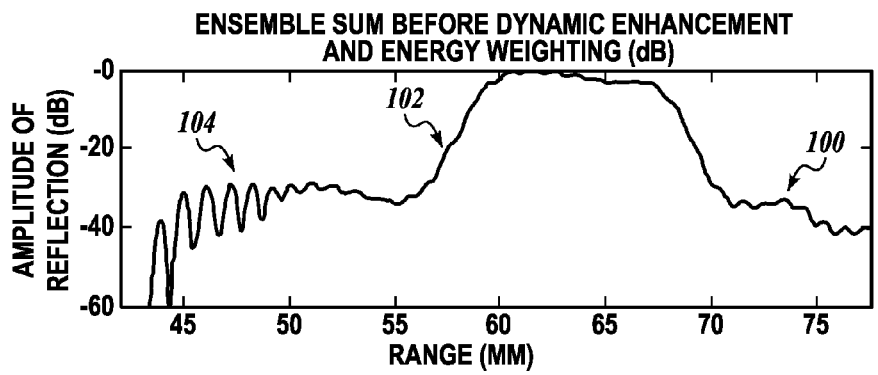
FIGS. 4E and 4F show a difference in the backscatter signals with and without weighting functions applied.

FIG. 4E illustrates an averaged backscatter signal 100 using the vectors shown in FIG. 4A without weighting by the weighting functions 80 and 90. As can be seen, there is significant noise in the signal at locations other than between 58-65 mm. where the variance in the backscatter signal is strongest. In the embodiment shown above, the leading edge of the averaged backscatter signal is detected and monitored as it moves toward the HIFU transducer. If the signal 100 were used, it would be difficult to distinguish between a leading edge 102 where the backscatter signal is strongest and a leading edge 104 that is noise.

Figure 4F:
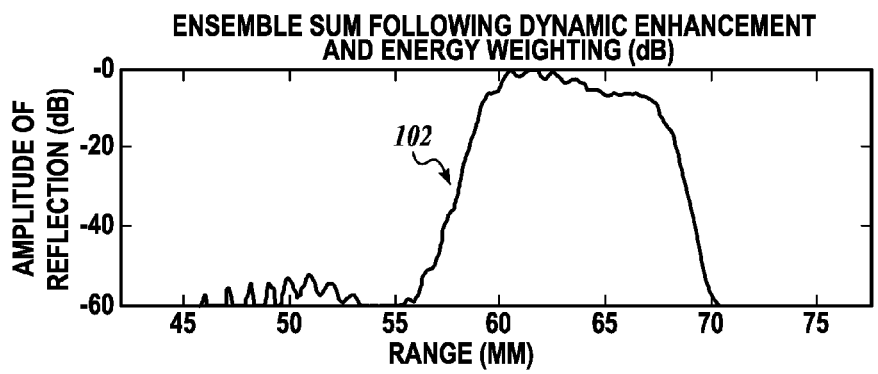

FIG. 4F shows the results of an averaged, weighted backscatter signal using the weighting functions 80, 90 described above applied to the vector data shown in FIG. 4A. As can be seen, the clutter in the signal is significantly reduced and there is a clear leading edge 102 of the signal where the changes in the amplitude of the backscatter signal are the greatest.

Figure 4G:
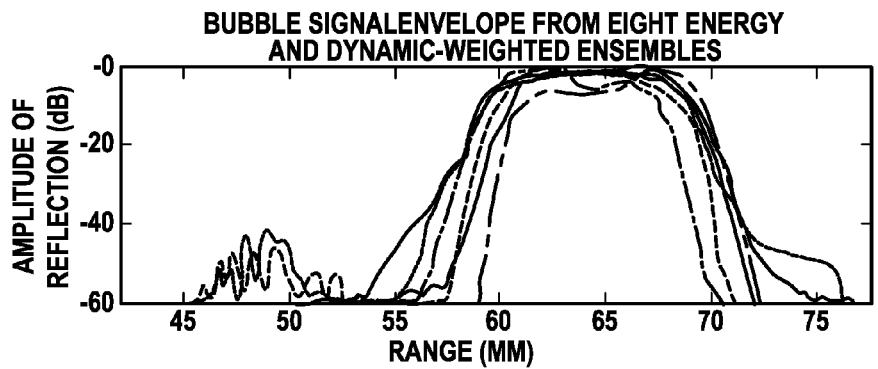
FIGS. 4G and 4H show a variability in multiple weighted, backscatter signals and backscatter signals that are weighted by their energy.

Even with weighting the backscatter signals, the variation in the averaged, weighted backscatter signals calculated for different groups of firings can be significant. FIG. 4G illustrates averaged, weighted backscatter signals calculated from 8 different groups of HIFU firings. To further remove clutter, one embodiment of the disclosed technology further weights an averaged, weighted backscatter signal by its own energy to emphasize those signals with large energy and deemphasize those signals with lower energy. To do this, the energy of each averaged weighted backscatter signal created from a group of firings is determined. The energies are normalized and each averaged, weighted backscatter signal is then further weighted by its own energy and the results are then averaged together.

Figure 4H:
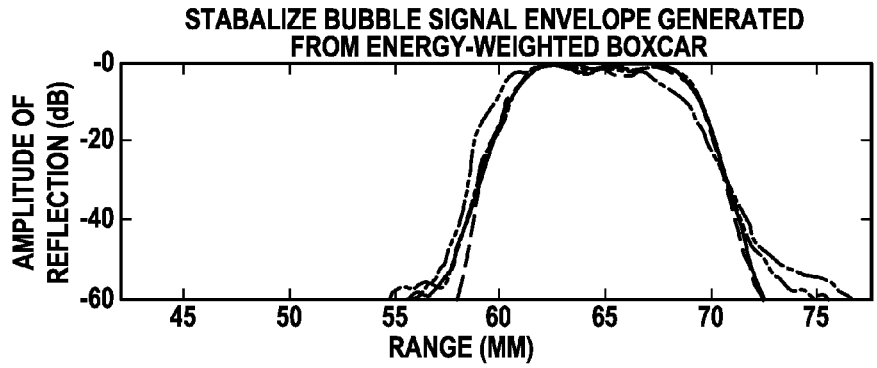

The result of this further weighting is shown in the graph of FIG. 4H. As can be seen in the graph, clutter in the region shallower than 58 mm. is significantly reduced and there is a very clean leading edge that can be used for bloom detection and monitoring.

Figure 5A:
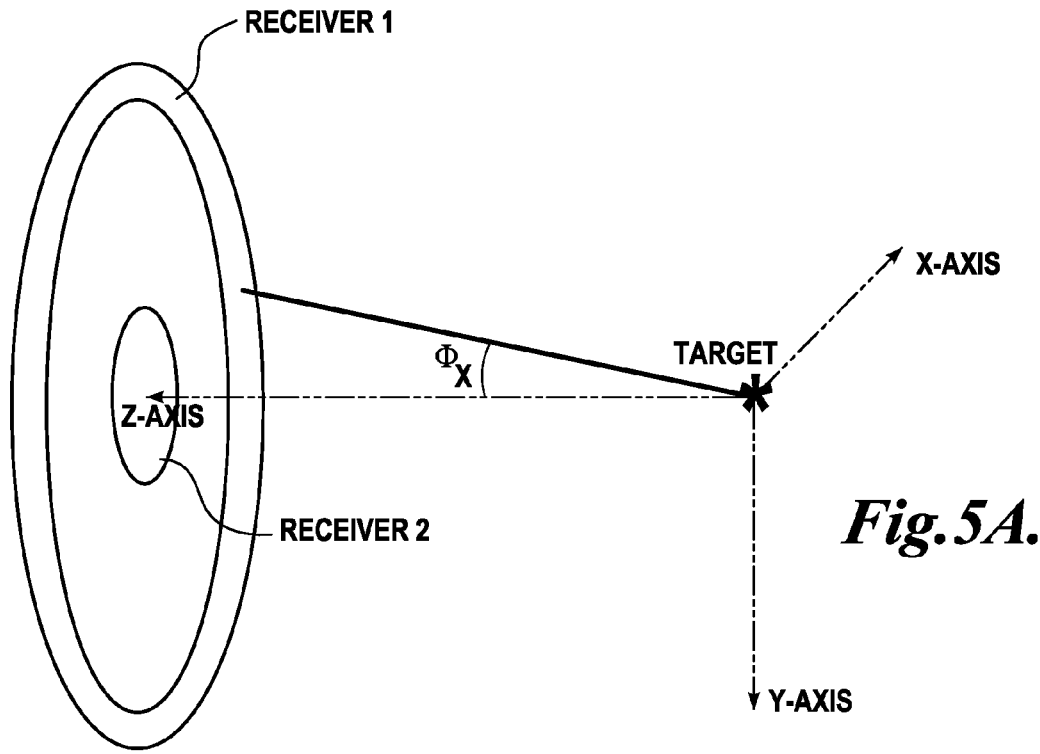
FIGS. 5A and 5B shows how the angular distribution of frequency components in a detected backscatter signal can vary with applied HIFU and can be used to control the HIFU treatment delivered in accordance with another embodiment of the disclosed technology.

In another embodiment of the disclosed technology, other features of the backscatter signal are used to generate a feedback signal that indicates treatment is complete. In the embodiment shown in FIGS. 5A and 5B, variations in angular distribution of frequency components within a backscatter signal can be used instead of the movement of leading edge to determine when treatment is complete. FIG. 5A illustrates an ultrasound detection system having two receivers, one on axis with the HIFU transducer and one off axis at angle Φ with respect to the treatment zone of the transducer. The amount energy detected at the off axis receiver will vary according to the equation:

$$E = \frac{\sin\left(kb\frac{\sin(\varphi_x)}{2}\right)}{\frac{kb\sin(\varphi_x)}{2}}$$

where b is the width of the reflecting surface, k is the wave number ($2\pi/\lambda$), and φ is the angle made between the therapy beam axis and the receiver directional vector to the target. In this equation, as frequency increases, the wavelength (λ) decreases and causes a reduction in the angular spread of the energy away from the beam axis. In other words, more high frequency energy is directed in front of the reflecting surface rather than to the sides. It is possible to measure the change in angular reflection and to correlate this to the amount of HIFU treatment completed.

Figure 5B:
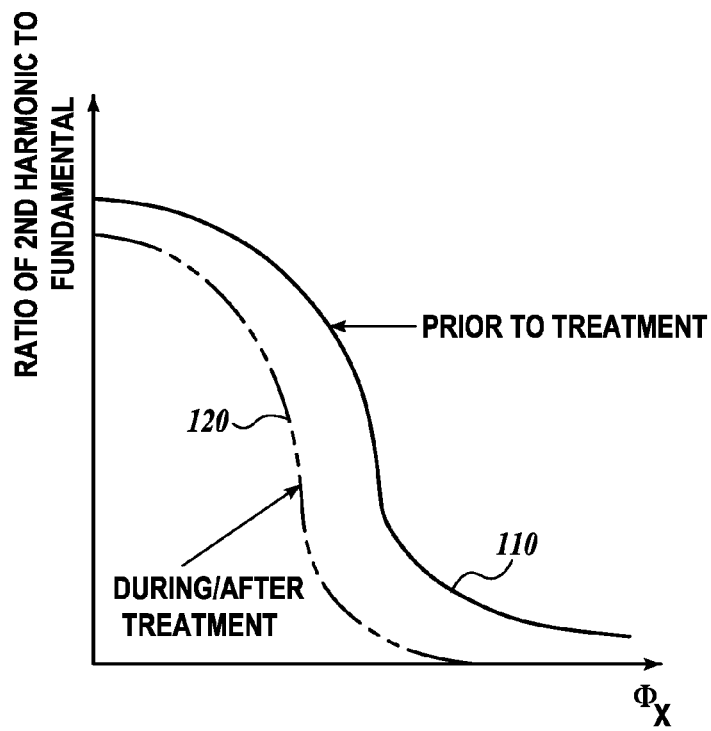

FIG. 5B shows a graph of how the angular distribution of a ratio (i.e. a second harmonic to the fundamental frequency of the HIFU signal) is expected to vary prior to treatment and during/after HIFU treatment. In this example, a curve 110 plots the ratio of the amount of second harmonic energy to the fundamental energy detected as a function of angle before treatment. A curve 120 plots the ratio of the second harmonic energy to the fundamental energy detected during or after treatment. Therefore, by either measuring the amount of harmonic energy detected at a certain angle or by determining the shift in the curve (i.e. determining the angle where a predetermined amount of harmonic energy is detected) it is possible to tell where the tissue is on the curves and therefore when treatment should be stopped. Shifts in the backscatter as a function of angle can be determined at multiple spatial locations. The particular relationship between energy, angle and amount of treatment may be stored in a computer readable memory based on previously determined clinical or theoretically derived data.

Figure 6:
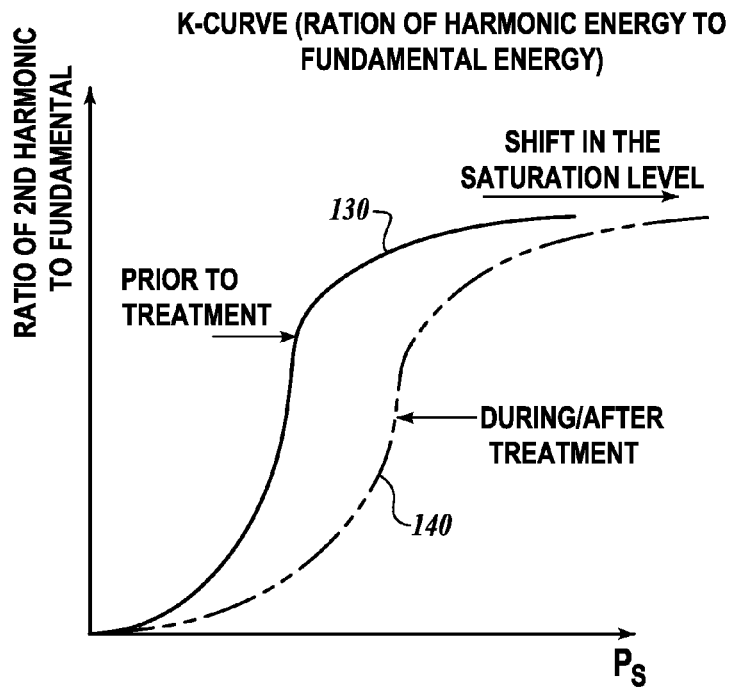
FIG. 6 shows variations in a power level required to saturate a characteristic of a received backscatter signal that can be used to control the HIFU treatment delivered in accordance with another embodiment of the disclosed technology.

In yet another embodiment, other characteristics of the tissue that change with applied HIFU are used to detect when the tissue is fully treated. FIG. 6 shows an example where the ratio of a harmonic (e.g. the second harmonic) to the HIFU fundamental frequency detected in a backscatter signal saturates with increases in HIFU transmit power. In this example, a curve 130 represents the saturation curve prior to treatment and a curve 140 represents the fact that increased energy will be required to achieve saturation in this same tissue location that is subjected to HIFU. To use the embodiment shown in FIG. 6, the initial curve 130 is determined by transmitting a number of test HIFU pulses at different power levels and detecting the amount of second harmonic energy and the fundamental energy in the backscatter signal. The ratio for multiple power levels is determined and forms the curve. Alternatively, the curve 130 could be recalled from a memory based on previously obtained or predicted data. During treatment, additional test HIFU pulses at different power levels are transmitted into the tissue, backscatter signals are detected and the ratio of harmonic to fundamental energy in the signal computed to produce the curve 140. Based on the differences between the curves 130 and 140, it can be determined when the tissue is fully treated based on previously determined relationships between the differences in the saturation curves and tissue treatment amounts. These shifts in the saturation can be computed at multiple spatial locations and monitored. For example shifts in the saturation curve may be only important outside of the treatment site.

Figure 7A:
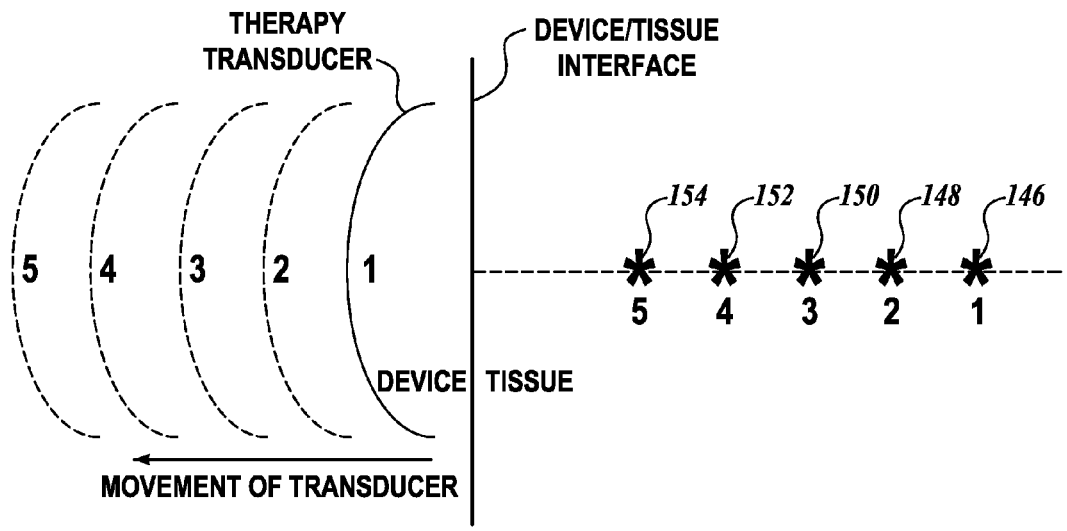
FIGS. 7A and 7B show how changes in attenuation can be determined and used to control the HIFU treatment delivered in accordance with another embodiment of the disclosed technology.
Figure 7B:
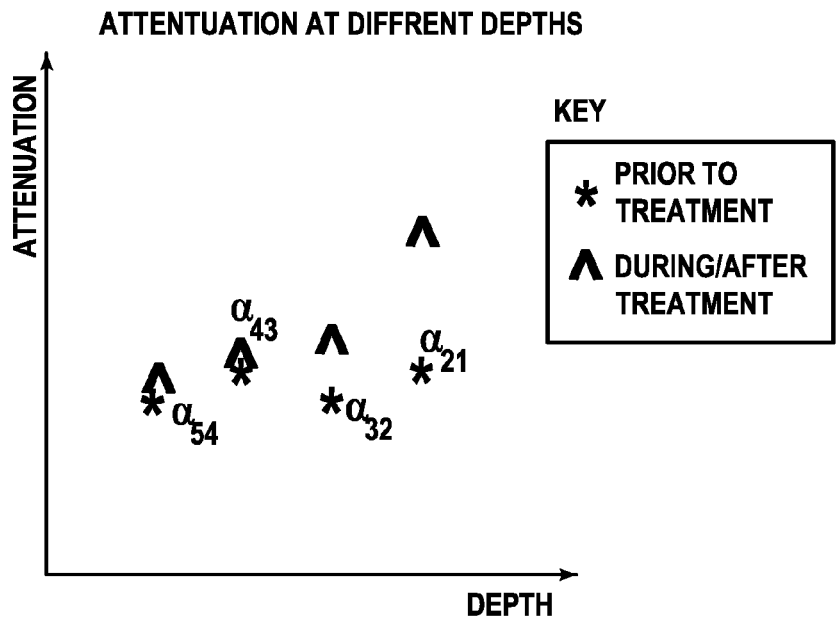

FIGS. 7A and 7B illustrate a further embodiment of the disclosed technology. In this embodiment, differences in attenuation that occur in tissue as a result of being treated with HIFU are used as a measure of when the tissue is fully treated. In the example shown in FIG. 7A, the amount of energy in a backscatter signal is detected at a number of different tissue depths 146, 148, 150, 152, 154 etc. HIFU signals can be directed at each depth either by moving the transducer if it has a fixed focus or adjusting the focus of the transducer if, for example, a transducer with electronic beamforming is used. The difference in the energy of the backscatter signal received from two adjacent depths is a measure of the attenuation of the tissue between those two depths. In the graph of FIG. 7B, the attenuation of each depth prior to treatment is determined and plotted. During treatment, the attenuation at each depth is again determined and plotted. A decision about when a treatment site is fully treated can be based on either when the attenuation at a specific depth in the tissue reaches a predetermined value or by when the attenuation value changes by more than some predetermined amount. The particular values of attenuation used to indicate fully treated tissue can be determined experimentally or theoretically.

Figure 8A:
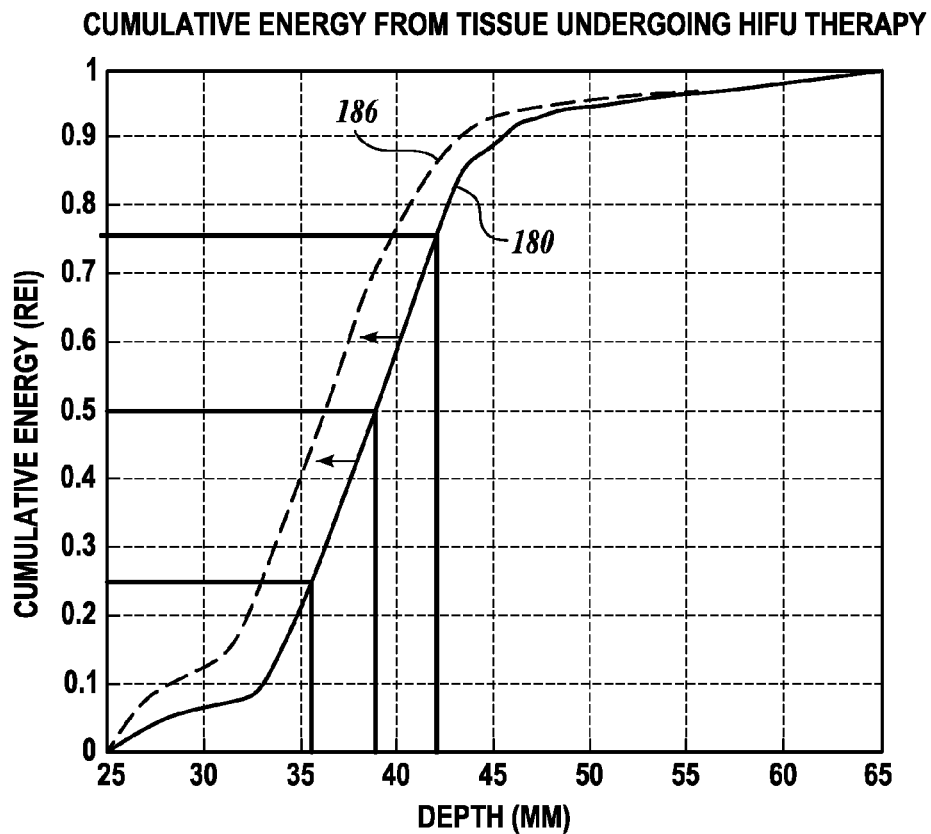
FIGS. 8A and 8B illustrate how a cumulative energy distribution function of a backscatter signal changes with applied HIFU and can be used to control the HIFU treatment delivered in accordance with another embodiment of the disclosed technology.
Figure 8B:
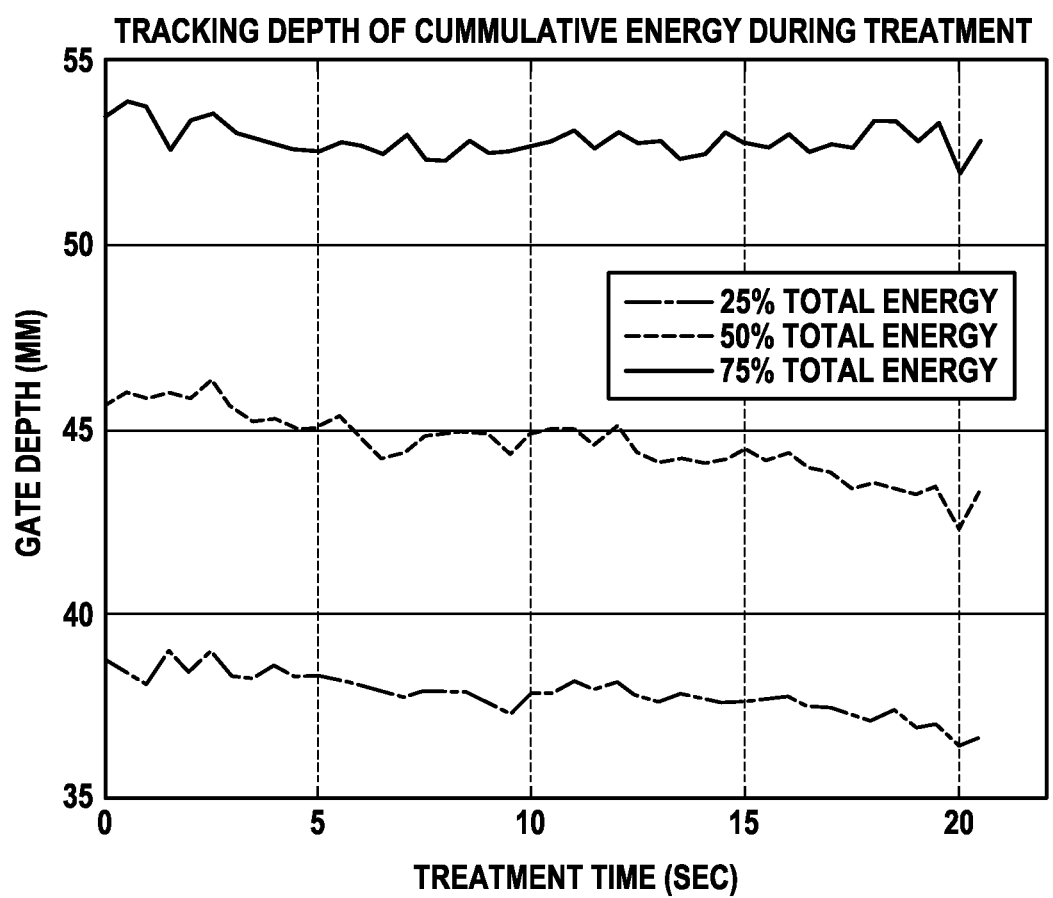

FIGS. 8A and 8B illustrate yet another technique for analyzing a characteristic of a backscatter signal to determine when tissue at a treatment site is fully treated. FIG. 8A shows a graph of the cumulative energy distribution function that is computed for a backscatter signal. As will be appreciated by those of skill in the art, a cumulative energy distribution function plots the depth at which a percentage of the total energy of the backscatter signal is contained. In one embodiment, the normalized, cumulative energy distribution function is determined by the formula:

$$C(x) = \frac{\int_{x_i}^{x} (p(r))^2 \, dr}{E_{total}}$$

In the example shown, a curve 180 shows that between the depths of 25 mm. and approximately 38 mm. 50% of the energy of the back scatter signal is contained. Between 25 mm. and 42 mm. approximately 75% of the energy of the backscatter signal is contained. As HIFU signals are applied to the tissue, the amount of energy contained at depths closer to the HIFU transducer will increase. For example, a curve 186 represents the cumulative energy distribution function of the tissue after or during treatment. The curve 186 shows that more energy is being deposited toward the HIFU transducer (i.e. the lesion is blooming).

FIG. 8B shows a plot of cumulative energy distributions taken at the 25%, 50% and 75% values versus treatment time. As can be seen, the depth for each energy level moves toward the HIFU transducer with increasing treatment time. To determine when a treatment site is fully treated, cumulative energy distribution functions can be computed for the backscatter signal created from each group of firings and either the value at a particular depth determined or the shift in the cumulative energy distribution function determined.

In the embodiments described above, only one change in a characteristic of the backscatter signal is used to determine when HIFU treatment is complete. However it should be appreciated that it is also possible to look at two or more changes in a characteristic (e.g. attenuation and cumulative energy distribution etc.) to determine when treatment is complete.

As indicated above, in one embodiment described above, the HIFU treatment signals are used as the interrogation signals that produce the backscatter signals used to detect a complete treatment. However, it is also possible to produce the interrogation signals with another transducer, such as an imaging transducer, or with the HIFU transducer operating at a lower power. Such interrogation signals can be delivered to the tissue after the HIFU therapy signals are delivered to the tissue. Changes occurring in the backscatter signals that are created in response to the interrogation signals can then be used to determine when treatment is complete. These interrogation signals can be comprised of either signals from the HIFU transducer or some other special-purpose interrogation transducer.

Although this invention has been described in connection with one or more preferred embodiments, those of ordinary skill in the art will understand that other embodiments fall within the scope of the description and claims. Note that throughout this document, the term "HIFU parameters" should be understood as inclusive of all variables related to control of HIFU and its tissue effects including (but not limited to): treatment duration, pulse duration, pulse repetition rate, frequency, peak and average power level, peak and average amplitude, duty cycle, motion of the treatment zone within targeted tissue, etc. Also, the terms "energy", "amplitude", or "power" should be considered interchangeable when assessing the scope of the description and claims contained herein. And the term "depth" should be considered to be interchangeable with "tissue depth", "distance from HIFU transducer", or "distance from HIFU treatment zone."

The embodiments of the invention in which an exclusive property or privilege is claimed are defined as follows:

1. A high intensity focused ultrasound (HIFU) system for treating tissue at a treatment site, the system comprising:
   a HIFU transducer and controller configured to deliver HIFU signals at a focus within a treatment site;
   a receiver configured to receive echo signals that result from delivery of the HIFU signals into the treatment site; and
   a processor that is programmed to detect energy in the received echo signals, integrate the detected energy over a determined time period and depth near the focus of the HIFU transducer, and based on the integrated energy in the echo signals, determine changes in a spatial distribution of energy in the treatment site,
   wherein the processor is further programmed to assess the spatial extent of the treatment site and produce a feedback control signal that is used to control the delivery of HIFU signals into the treatment site based on the determined changes in the spatial distribution of energy in the treatment site.

2. The system of claim 1, wherein the processor is further programmed to detect movement of a leading edge of the received echo signals toward the HIFU transducer.

3. The system of claim 1, wherein the processor is further programmed to process the echo signals to emphasize variations in the echo signals.

4. The system of claim 1, wherein the processor is further programmed to produce an averaged echo signal from a number of the received echo signals, wherein the received echo signals are weighted to emphasize depths in the treatment site away from the HIFU transducer within the received echo signals that exhibit variances in amplitude.

5. The system of claim 4, wherein the processor is programmed to weight the received echo signals with the energy of the received echo signals to emphasize the received echo signals with greater energy and deemphasize the received echo signals with lower energy.

6. The system of claim 1, further comprising a mechanism configured to steer the focus of the HIFU transducer around a perimeter of an elemental treatment volume, wherein the processor is programmed to detect changes in the spatial distribution of energy in the treatment site as the focus is moved along the perimeter of the elemental treatment volume.

7. The system of claim 1, wherein the processor is programmed to supply the feedback control signal to the HIFU controller to modify the delivery of HIFU signals into the treatment site.

8. The system of claim 1, wherein the processor is programmed to supply the feedback control signal to a human-perceivable alarm.

9. The system of claim 1, further comprising a transducer configured to deliver an interrogation signal to the treatment site, wherein the processor is further programmed to process echo signals that result from delivery of the interrogation signal to the treatment site.

10. A high intensity focused ultrasound (HIFU) system for treating tissue at a treatment site, the system comprising:
    a HIFU transducer and controller configured to deliver HIFU signals at a focus within a treatment site;
    a receiver configured to receive echo signals that result from delivery of the HIFU signals into the treatment site; and
    a processor that is programmed to detect changes in an angular distribution of frequency components in the received echo signals, wherein based on the detected changes in the angular distribution, the processor is further programmed to assess the spatial extent of the treatment site and produce a feedback control signal that is used to control the delivery of HIFU signals into the treatment site.

11. The system of claim 10, wherein the processor is further programmed to produce an averaged echo signal from a number of the received echo signals, wherein the received echo signals are weighted to emphasize depths away from the HIFU transducer within the received echo signals that exhibit variances in amplitude.

12. The system of claim 11, wherein the processor is programmed to weight the received echo signals with the energy of the received echo signals to emphasize the received echo signals with greater energy and deemphasize the received echo signals with lower energy.

13. The system of claim 10, further comprising a mechanism configured to steer the focus of the HIFU transducer around a perimeter of an elemental treatment volume, wherein the processor is programmed to detect changes in the angular distribution of frequency components in the received echo signals as the focus is moved along the perimeter of the elemental treatment volume.

14. A high intensity focused ultrasound (HIFU) system for treating tissue at a treatment site, the system comprising:
 a HIFU transducer and controller configured to deliver HIFU signals at a focus within a treatment site;
 a receiver configured to receive echo signals that result from delivery of the HIFU signals into the treatment site; and
 a processor that is programmed to detect changes in a power level required to saturate a characteristic of the echo signals, wherein based on the detected changes in the power level, the processor is further programmed to assess the spatial extent of the treatment site and produce a feedback control signal that is used to control the delivery of HIFU signals into the treatment site.

15. The system of claim 14, wherein the processor is further programmed to produce an averaged echo signal from a number of the received echo signals, wherein the received echo signals are weighted to emphasize depths away from the HIFU transducer within the received echo signals that exhibit variances in amplitude.

16. The system of claim 15, wherein the processor is programmed to weight the received echo signals with the energy of the received echo signals to emphasize the received echo signals with greater energy and deemphasize the received echo signals with lower energy.

17. The system of claim 14, further comprising a mechanism configured to steer the focus of the HIFU transducer around a perimeter of an elemental treatment volume, wherein the processor is programmed to detect changes in the power level required to saturate a characteristic of the received echo signals as the focus is moved along the perimeter of the elemental treatment volume.

* * * * *